United States Patent [19]

Hartig et al.

[11] 4,261,900
[45] Apr. 14, 1981

[54] PREPARATION OF TETRAHYDROFURAN

[75] Inventors: Juergen Hartig, Gruenstadt; Hans-Martin Weitz, Bad Durkheim, both of Fed. Rep. of Germany

[73] Assignee: BASF Aktiengesellschaft, Fed. Rep. of Germany

[21] Appl. No.: 101,629

[22] Filed: Dec. 10, 1979

[30] Foreign Application Priority Data

Dec. 28, 1978 [DE] Fed. Rep. of Germany ....... 2856455

[51] Int. Cl.$^3$ ............................................ C07D 307/08
[52] U.S. Cl. ................................................ 260/346.11
[58] Field of Search .................................... 260/346.11

[56] References Cited

U.S. PATENT DOCUMENTS 4,010,171 3/1977 Smith .............................. 260/346.11
4,080,366 3/1978 Smith .............................. 260/346.11
4,124,600 11/1978 Jenkins, Jr. ....................... 260/346.11

FOREIGN PATENT DOCUMENTS 1170222 11/1969 United Kingdom .

Primary Examiner—Henry R. Jiles
Assistant Examiner—Bernard Dentz
Attorney, Agent, or Firm—Keil & Witherspoon

[57] ABSTRACT

A process for the preparation of tetrahydrofuran by heating a carboxylic acid diester of butane-1,4-diol in the gas phase at above about 160° C. in the presence of an aluminum oxide catalyst which is obtained by drying, at 70°–120° C., an aluminum hydroxide gel which has been precipitated from an aqueous aluminum sulfate solution by means of a basic agent.

2 Claims, No Drawings

PREPARATION OF TETRAHYDROFURAN

It is known that tetrahydrofuran (THF) can be prepared by a number of different processes, amongst which the dehydration of butane-1,4-diol, and the catalytic hydrogenation of furan, are particularly important. Most tetrahydrofuran is in fact prepared by a multistage process, starting from the reaction of acetylene with formaldehyde to form butynediol, and followed by hydrogenation of the latter to butanediol, which in turn is dehydrated to tetrahydrofuran.

In addition, tetrahydrofuran can be obtained by catalytically hydrogenating maleic acid, fumaric acid and succinic acid, their anhydrides and ester derivatives, and also by catalytic hydrogenation of butyrolactone.

More recently, carboxylic acid esters of butane-1,4-diol have become industrially available from a variety of processes, and these esters can also be converted to tetrahydrofuran, namely by dehydroacyloxylation, ie. elimination of the carboxylic acid, accompanied by etherification.

Proposals for such processes are to be found, for example, in British Pat. No. 1,720,222 and German Laid-Open Application No. DOS 2,653,136.

These proposals relate both to liquid phase reactions and vapor or gas phase reactions. Catalysts mentioned are, inter alia, aluminum oxide, silica and mixed oxides containing these.

It appears that aluminum oxide does not prove particularly successful, because German Laid-Open Application No. DOS 2,653,136 proposes to use aluminum oxide containing tungsten oxide to achieve an improvement.

We have in fact found that commercial aluminum oxides conventionally used as catalysts or recommended for this purpose are not very suitable, or even quite unsuitable, for the preparation of THF from butanediol diacetate.

We have now found the process specified in claim 1, which is based on the use of an aluminum oxide prepared by a specific method.

It is to be remembered that aluminum hydroxides can be precipitated from acid or basic solution, and that these methods in the first place produce gels which on heating undergo gradual dehydration and finally crystallize as various modifications of aluminum oxide. Furthermore, the acid anion plays an important part in whether efficient catalysts are obtained, since precipitation from nitric acid solution does not give advantageous catalysts, in contrast to precipitation from sulfuric acid solution in accordance with the present invention.

As the determination of the surface area of such oxides shows, the products are in all cases microcrystalline modifications, mostly with numerous crysal defects and, furthermore, contaminated (modified) in a specific way resulting from their process of preparation.

The catalysts are thus obtained by precipitating an aqueous aluminum sulfate solution with a basic agent, eg. a hydroxide or carbonate of an alkali metal or alkaline earth metal, ammonia or a basic ammonium salt, and heating the precipitate at from 70° to 120° C. Preferred basic agents of the above type are weakly basic agents, such as carbonates, in particular ammonium carbonate. The aluminum hydroxide gel is preferably dried at from 80° to 110° C. under reduced pressure.

As regards the use of the catalysts in the process in question, the following details may be noted:

Esters of butanediol, for the purposes of the present invention, are in the main the esters of formic acid, acetic acid and propionic acid. For economic reasons, the esters of higher fatty acids are not particularly important.

The reaction in the gas phase commences to a significant extent at 175° C.; because of the boiling point of the ester under atmospheric pressure, the reaction is in general carried out at from 200° to 320° C., preferably from 280° to 320° C. Slightly superatmospheric pressure, for example up to 5 bar, may in certain cases make it possible to reduce the size of the apparatus, provided the temperature is sufficiently high to ensure that the ester is nevertheless in the gas phase.

The catalyst may be used as a fixed bed or fluidized bed.

The reaction is carried out in the presence of not less than 1 mole of steam per mole of ester; it is advantageous to use an excess of up to 15 moles of steam.

The reaction gases are worked up in a conventional manner; in some cases, it may be desirable to employ incomplete conversion, with recycling of starting material, but the virtually complete conversion which, according to the invention, is easily achievable is to be preferred.

EXAMPLE A

PREPARATION OF A CATALYST NOT ACCORDING TO THE INVENTION 1 mole (374.1 g) of aluminum nitrate ($Al(NO_3)_3.9-H_2O$) are dissolved in 1.5 kg of distilled water and the solution is heated at 60° C. in a 6 liter stirred flask. 300.3 g of ammonium carbonate are dissolved in 1.78 kg of distilled water and this solution is added gradually, in the course of 50 minutes, to the aluminum nitrate solution, whilst stirring. When all has been added, the solution has a pH of 7.5. The precipitate formed is centrifuged off and is three times suspended in 0.5 kg of water and centrifuged off in each case. It is then dried for 12 hours at 100° C. under a waterpump vacuum, comminuted and dried for a further 18 hours. The dry residue (87 g) is recomminuted and a particle size fraction corresponding to from 0.1 to 0.5 mm mesh width is sieved out.

EXAMPLE B

PREPARATION OF A CATALYST ACCORDING TO THE INVENTION

The procedure described in Example 1 is followed, but 1 mole (666.4 g) of aluminum sulfate ($Al_2(SO_4)_3.18-H_2O$) is dissolved in 1.2 kg of distilled water and a solution of 592.0 g of ammonium carbonate in 2.5 kg of distilled water is added in the course of 60 minutes to the aluminum sulfate solution at 60° C. Ultimately, 184.1 g of residue are obtained from which a particle size fraction of from 0.1 to 0.5 mm is obtained by sieving.

EXAMPLE 1

20 g of the catalyst from Example B are introduced into a vertical quartz reaction tube (length 160 mm, diameter 62 mm) which serves as a model of a fluidized bed reactor. At the lower end of the tube is a quartz frit, and at the upper end of the tube a descending line leads to a downstream condenser, separator and cold trap. Per hour, 120 ml (125 g) of butane-1,4-diol diacetate and 34.2 ml of water (molar ratio of diacetate to H$_2$O=1:2.65) are evaporated and passed, at 285°-300° C., into the bottom of the reactor. After 115 minutes, the experiment is discontinued. 302.2 g of liquid reaction product, containing 19.23% by weight of THF and 32.07% by weight of butanediol diacetate, are obtained. 4.16 millimoles of butadiene are isolated from the off-gas. Accordingly, the conversion of butanediol diacetate is 59.5 mole %; the conversion to THF is 58.7 mole % and the conversion to butadiene 0.3 mole %, ie. the yield of THF, based on material converted, is 98.6%.

COMPARATIVE EXPERIMENT

The reactor is filled with 20 g of catalyst prepared as described in Example A. 261 ml (271.4 g) of butanediol diacetate and 84 g of water (molar ratio 1:3) are introduced at 292°-307° C. in the course of 2 hours. 304.5 g of liquid reaction product containing 69.8 g of diacetate and 10 g of THF are obtained. 28.8 g of butadiene are isolated from the cold trap. The conversion of butanediol diacetate is 74.3% but the conversion to THF is only 8.8%.

We claim:

1. In a process for the preparation of tetrahydrofuran by heating a carboxylic acid diester of butane 1,4-diol in the gas phase at above about 160° C. in the presence of at least an equimalar amount of steam and an aluminum oxide catalyst, the improvement which comprises: using as the aluminum oxide catalyst one which has been obtained by drying, at 70°-120° C., an aluminum hydroxide gel precipitated from an aqueous aluminum sulfate solution by means of a basic agent.

2. The process of claim 1, wherein an aluminum oxide catalyst is used which has been prepared by heating the aluminum hydroxide gel at 80°-110° C. under reduced pressure.

* * * * *